(12) United States Patent
Cullum et al.

(10) Patent No.: US 7,242,470 B2
(45) Date of Patent: Jul. 10, 2007

(54) MULTILAYERED SURFACE-ENHANCED RAMAN SCATTERING SUBSTRATES

(75) Inventors: Brian M. Cullum, Laurel, MD (US); Honggang Li, Baltimore, MD (US)

(73) Assignee: University of Maryland at Baltimore County, Baltimore, MD (US)

( * ) Notice: Subject to any disclaimer, the term of this patent is extended or adjusted under 35 U.S.C. 154(b) by 172 days.

(21) Appl. No.: 11/187,300

(22) Filed: Jul. 22, 2005

(65) Prior Publication Data

US 2006/0017918 A1    Jan. 26, 2006

Related U.S. Application Data

(60) Provisional application No. 60/590,775, filed on Jul. 23, 2004.

(51) Int. Cl.
*G01J 3/44* (2006.01)
*G01N 21/65* (2006.01)

(52) U.S. Cl. .................................................. 356/301
(58) Field of Classification Search ................. 356/301
See application file for complete search history.

(56) References Cited

OTHER PUBLICATIONS

Mulvaney et al., Three-Layer Substrates for Surface-Enhanced Raman Scattering: Preparation and Preliminary Evaluation, Jounal of Raman Spectroscopy, 2003, vol. 43, pp. 163-171.*
Dick et al., Metal Film over Nanosphere (MFON) Electrodes for Surface-Enhanced Raman Spectroscopy (SERS): Improvements in Surface Nanostructure Stability and Suppression of Irreversiable Loss, J. Phys. Chem. B, 2002, vol. 106, pp. 853-860.*

* cited by examiner

*Primary Examiner*—F. L. Evans
(74) *Attorney, Agent, or Firm*—Benjamin Aaron Adler

(57) ABSTRACT

Provided herein are dual- and multi-layer metal film over nanostructure substrates. These Dual-FON and Multi-FON SERS substrates comprise a rough nanostructured layer and two or more SERS-active metal film layers deposited thereon with a layer of dielectric between the metal film layers. Also provided is a method of increasing the intensity of a Raman signal during surface enhanced Raman spectroscopy using the SERS substrates and a method of fabricating these Dual- or Multi-FON SERS substrates.

30 Claims, 8 Drawing Sheets

MULTILAYERED SURFACE-ENHANCED RAMAN SCATTERING SUBSTRATES

CROSS-REFERENCE TO RELATED APPLICATION

This non-provisional application claims benefit of priority to provisional U.S. Ser. No. 60/590,775, filed Jul. 23, 2004, now abandoned.

BACKGROUND OF THE INVENTION

1. Field of the Invention

This invention relates generally to the fields of Raman spectroscopy and spectroscopic imaging. Specifically, the present invention relates to dual- and multilayered substrates useful in surface enhanced Raman spectroscopic applications.

2. Description of the Related Art

Surface enhanced Raman scattering (SERS) has been used to monitor the presence of chemical species for a wide variety of applications, including: medicine, biochemical research), electrochemistry ultrahigh vacuum science (UHV) environmental monitoring and many others (1–11). The main reason for its widespread application arises from its ability to provide structural information about the analyte being measured, while also permitting trace analyses, i.e., single molecule/particle detection in some cases (12–14). Detection of trace amounts of analyte is due to the large signal enhancements achieved with SERS, typically $10^3$–$10^6$, as compared to spontaneous Raman scattering. While an exact description of the SERS phenomenon is complex and not completely understood, it is well known that the large SERS enhancement factors, achieved by placing the analyte of interest in contact with a roughened metal surface, occur primarily through a combination of a chemical enhancement mechanism and an electromagnetic enhancement mechanism (15–17).

Chemical enhancement arises from the interaction of the analyte with the metal surface upon adsorption. This results in a charge transfer between the metal and adsorbate, resulting in an overlap of the transition wave functions of the metal and analyte. Therefore, for chemical enhancement, direct contact between the metal surface and the analyte is required. Electromagnetic enhancement is attributed to an increased electromagnetic field near the metal surface due to surface plasmon resonance (SPR). Upon excitation of the substrate with the appropriate wavelength of light, metal conduction electrons are excited to collective oscillation by the incident oscillating electromagnetic wave of excitation light. This oscillation provides an increased interaction between the metal surface and the electron cloud of the analyte molecule and is believed to account for the majority of the signal enhancement for most analyses (18).

In an attempt to take advantage of the potentially large signal enhancement factors associated with SERS, many different types of substrates have been developed. These substrates are typically made of silver, gold or copper and, in rare cases, alkali and transition metals (19–20). Some of the most commonly employed SERS substrates include noble metal colloids (21–22) electrochemically roughened electrodes (23–25), acid-etched metal foils (26), chemically produced silver island films (27–29) vapor deposited metal island films (30), and silver films over nanoparticles/nanostructures (SFONnn) (9, 31–34).

Metal colloids typically provide the greatest SERS enhancements factors. In fact, in specific cases, colloidal silver substrates have been reported to be capable of single molecule detection (12–13, 35). However, SERS analyses performed using these metal colloidal substrates demonstrate poor stability over time, as the colloidal particles tend to aggregate and precipitate in solution, thereby changing the morphological as well as chemical properties of the substrate. In addition, inhomogeneous enhancement is present throughout the sample due to the random distribution and aggregation of the colloidal particles.

Metal island film substrates are capable of providing significant SERS enhancement factors, while reducing the problems associated with aggregation and precipitation in metal colloidal substrates. Metal island film substrates provide a significantly greater spot-to-spot reproducibility than colloidal substrates and are relatively simple to fabricate. Unfortunately, enhancements obtained from this type of substrate are significantly less than those obtained from colloidal substrates and analytical studies are complicated by the need to accurately control the deposition parameters that influence the islands' size, shape and spacing distribution (36). Recently, a method of preparing dual-layered metal island film substrates that are capable of significant signal enhancements relative to conventional single layer silver island films, making them much more sensitive has been developed and characterized (37). Substrates were prepared by coating 75 nm of silver on a surface to form a layer of discrete silver islands. The silver islands were exposed to air and a second silver island layer of a 45 nm thickness was deposited on top of the previous layer. Scanning electron microscope images of these substrates revealed that the second layer of silver islands were deposited selectively on underlying silver islands creating an optimal surface morphology, both size and shape, for SERS. Using these substrates, SERS signal enhancement factors of $10^4$, as compared to spontaneous Raman scattering, were achieved.

A three-layered substrate that combines aspects of colloidal substrates with the lifetime stability and reproducibility of silver film over nanostructure (SFON) based substrates has been developed (38–39). The substrates were prepared by placing 12 nm diameter colloidal gold (Au) nanoparticles on a glass support and chemically coating them with silver (Ag) before thermally evaporating a layer of silver islands on top of the chemically deposited silver. This process created substrates that had well controlled and distributed colloidal particles with a silver coating from the chemical deposition as well as silver islands between the colloidal particles to reduce fluorescence background signals from impurities deposited during the chemical reduction process. These substrates also exhibited enhancement factors on the order of $7\times10^4$, as well as an enhanced reproducibility of 15%, compared to colloidal substrates. In both of these previous studies, multiple layers of noble metals were used to carefully construct roughened metal surfaces with precisely controlled surface morphologies which were attributed as the primary reason for the enhanced electromagnetic field and the increased reproducibility.

Accordingly, a need in the art is recognized for improved surface enhanced Raman spectroscopic substrates effective to increase a SERS signal. More specifically, the prior art is deficient in surface enhanced Raman spectroscopic substrates comprising at least two or more continuous SERS-active metal layers deposited thereon. The present invention fulfills this longstanding need and desire in the art.

SUMMARY OF THE INVENTION

The present invention is directed to a substrate for surface enhanced Raman spectroscopy (SERS). The SERS substrate comprises a support material having a flat surface that is coated with a plurality of nanostructures, two or more layers of a SERS-active metal deposited thereon and one or more layers of a dielectric on one or more layers of the SERS-active metal.

The present invention also is directed to a system for surface enhanced Raman spectroscopy (SERS). The SERS system comprises the SERS substrate described herein, a radiation source having optical power effective to penetrate the SERS-active metal layers of the SERS substrate; a spectrometer effective for collecting and dispersing collimated back scattered Raman radiation, and a detector for detecting the dispersed radiation. The SERS system also has a first set of optics for directing incident radiation from the radiation source to one or more SERS-active metal surfaces comprising the substrate and a second set of optics for collimating and directing back scattered Raman radiation emitted from the substrate to the spectrometer. The present invention is directed to a related SERS system further comprising a means for analyzing and displaying the detected Raman radiation as a Raman spectral image.

The present invention is directed further to a method for increasing a Raman signal intensity during surface-enhanced Raman spectroscopy (SERS). The method comprises providing the SERS substrate described herein, bringing an analyte into effective contact with the SERS substrate and illuminating the analyte with radiation from a source of sufficient power to optically penetrate the SERS-active metal layers comprising the SERS substrate thereby producing an increase in the Raman signal intensity emitted therefrom. In the method the increase in SERS signal intensity is a result of the total increase in electromagnetic field within said SERS-active metal layers. The present invention is directed to a related method further comprising collecting and detecting the increased Raman signal for spectral analysis thereof and generating a signature spectrum for the analyte based on the spectral analysis.

The present invention is directed further still to a method of fabricating a substrate for surface-enhanced Raman spectroscopy (SERS). The method comprises coating a support surface with a plurality of nanostructures suitable for a SERS application and depositing a continuous layer of SERS-active metal over said nanostructures. The the SERS-active metal layer is covered with a dielectric and a continuous layer of the SERS-active metal is deposited over the dielectric. The method steps of covering the deposited continuous layer with a dielectric and depositing a continuous SERS-active metal layer thereon may be repeated.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
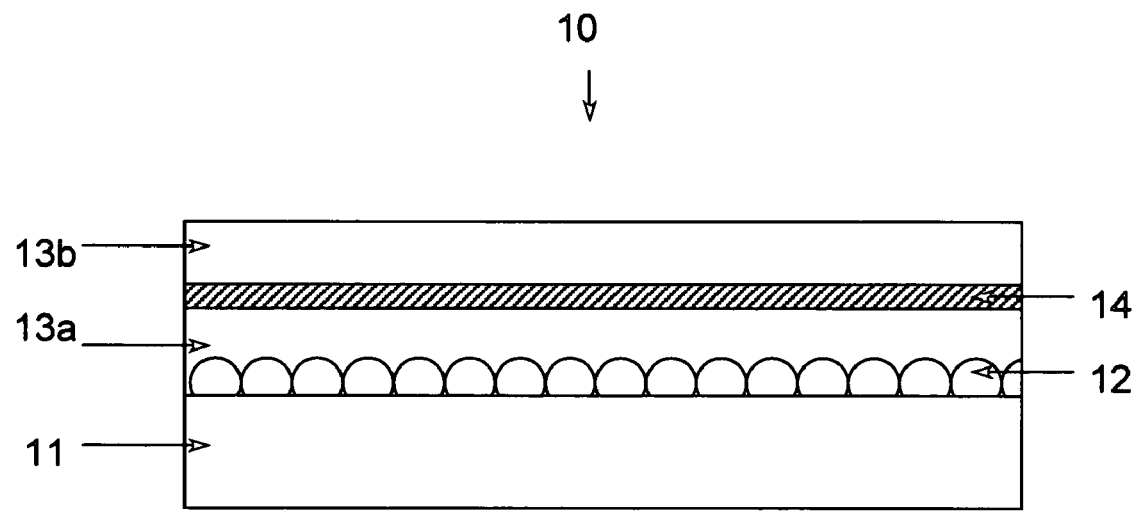
FIGS. 1A–1C depict Dual-FON (FIG. 1A) and a Multi-FON (FIG. 1B) substrates and a surface enhanced Raman spectroscopic (SERS) system (FIG. 1C) using the substrates.

In one embodiment of the present invention there is provided a substrate for surface enhanced Raman spectroscopy (SERS), comprising a support material having a flat surface coated with a plurality of nanostructures; two or more layers of a SERS-active metal deposited thereon; and one or more layers of a dielectric on one or more layers of said SERS-active metal.

In this embodiment the support surface may be glass, quartz, metal foil, paper, a plastic surface, or wood. Also, the nanostructures may be alumina nanoparticles, silica spheres, titanium spheres, organic polymer spheres, or nanotubes. The nanostructures may have a diameter of about 10 nm to about 10,000 nm.

In addition, in this embodiment the SERS-active metal may be silver, gold, platinum, copper, ruthenium, rhodium, iron, or alkali metal. The SERS substrate may comprise two to five SERS-active metal layers and one to four dielectric layers. Furthermore, each SERS-active metal layer may have a thickness of about 25 nm to about 1000 nm. Alternatively, the total thickness of the SERS-active metal layers may be about 50 nm to about 10,000 nm.

Furthermore, in this embodiment the dielectric may be an oxide of a SERS-active metal, silicon dioxide, titanium dioxide, or organic polymers. In aspects of this embodiment the dielectric may be formed via exposure of the SERS-active metal to air under ambient conditions, via vapor deposition or via chemical deposition. Exposure of the SERS-active metal to form the dielectric thereon is metal dependent such that exposure ranges from seconds to months.

In another embodiment of the present invention there is provided a system for surface enhanced Raman spectroscopy (SERS), comprising the SERS substrate described supra; a radiation source having optical power effective to penetrate the SERS-active metal layers of the SERS substrate; a spectrometer effective for collecting and dispersing collimated back scattered Raman radiation; a detector for detecting the dispersed radiation; a first set of optics for directing incident radiation from the radiation source to one or more SERS-active metal surfaces comprising the substrate; and a second set of optics for collimating and directing back scattered Raman radiation emitted from the substrate to the spectrometer. Further to this embodiment the SERS system may comprise means for analyzing and displaying the detected Raman radiation as a Raman spectral image.

In these embodiments the radiation source may be a laser producing about 1 µW of power to about 5 W of power. Also, the detector may be an intensified charge coupled device, a photomultiplier tube, a photodiode or a photodiode array. In addition, the first set of optics and the second set of optics may comprise means to collimate radiation and one or more filters or lenses operably disposed between the radiation source, the SERS substrate and the spectrometer.

In yet another embodiment of the present invention there is provided a method for increasing a Raman signal intensity during surface-enhanced Raman spectroscopy, comprising providing the SERS substrate described supra; bringing an analyte into effective contact with the SERS substrate; and illuminating the analyte with radiation from a source of sufficient power to optically penetrate the SERS-active metal layers comprising the SERS substrate to increase a SERS signal intensity emitted therefrom; where the increase in signal intensity is a result of the total increase in electromagnetic field within said SERS-active metal layers. Further to this embodiment the method comprises collecting and detecting the increased SERS signal for spectral analysis thereof and generating a signature spectrum for the analyte based on the spectral analysis. In these embodiments the radiation source may be a laser producing about 1 µW of power to about 5 W of power.

In still another embodiment of the present invention there is provided a method of fabricating a substrate for surface-enhanced Raman spectroscopy (SE-RS), comprising coating a support surface with a plurality of nanostructures suitable for a SERS application; depositing a continuous layer of a SERS-active metal over the nanostructures; covering the deposited continuous layer with a dielectric; and depositing a continuous layer of the SERS-active metal over the dielectric. Further to this embodiment the method may comprise repeating the steps of covering the deposited continuous layer with a dielectric and depositing a continuous SERS-active metal layer thereon. In this further embodiment the steps may be repeated one to three times.

In one aspect of these embodiments wherein covering the SERS-active metal layer with a dielectric comprises exposing the SERS-active metal layer to air at ambient conditions to form a dielectric thereon or depositing the dielectric via vapor deposition or chemical deposition. For example exposure of the SERS-active metal to form the dielectric thereon is metal dependent such that exposure ranges from seconds to months. In these embodiments the support surface, the nanostructures, SERS active metals, the dielectric, and the diameters or thicknesses thereof are as described supra.

The present invention provides dual-layer (Dual-FON) and multi-layer (Multi-FON) film over nanostructure SERS substrates that have thick continuous layers of a SERS-active metal separated by a dielectric. These continuous dual- and multi-layer FON substrates provide as much as 1000% signal enhancement compared to silver film over nanostructure (SFON) substrates containing one layer of silver of the same total thickness and same surface morphology. In addition, these multilayered substrates exhibit significantly greater lifetimes following exposure to ambient conditions than SFON substrates or silver island film-based substrates and enhanced reproducibility from spot-to-spot as well as from substrate-to-substrate.

The surface morphology of Dual-FON and Multi-FON substrates provides a dual- or multi-layer surface plasmon resonance that is the main contributory factor to the enhancements observed over single layer SFON substrates. This enhancement is consistent with an electromagnetic enhancement from the additional under-layers of SERS-active metal that are separated by a dielectric and does not require a specific surface morphology. It is contemplated that a wide variety of appropriately sized nanostructured support materials could be used to fabricate Dual-FON and Multi-FON substrates.

The SERS substrates are fabricated on a support surface coated with nanostructures suitable for a SERS application. Two or three or more continuous layers of a SERS-active metal are deposited thereon. A dielectric is disposed between metal layers. It is also contemplated that additional metal layers can be applied to achieve even greater signal enhancements, as long as sufficient excitation power exists to optically penetrate these additional layers, potentially providing solid SERS substrates with enhancement factors similar to colloidal suspensions.

The present invention also provides a system for improved surface enhanced Raman spectroscopy using the Dual-FON and Multi-FON substrates provided herein. Generally, the SERS system comprises a radiation source, a SERS substrate, a spectrometer and a detector. The radiation source, the spectrometer and the detector are all commercially available components.

Generally, the radiation source may be a laser emitting radiation in the UV to the IR range or any other suitable excitation source for SERS analysis. Some examples of commonly used lasers include argon ion lasers emitting wavelengths of 448 nm or 514.5 nm, krypton ion lasers emitting wavelengths of 530.9 nm or 647.1 nm, HeNe lasers emitting wavelength of 632.8 nm, diode lasers emitting wavelengths of 782 nm or 830 nm, or Nd/YAG lasers for wavelengths of 1064 nm.

The SERS system also comprises optics to direct radiation from the radiation source to the SERS substrate and the back scattered radiation from the SERS substrate to the spectrometer. The optics, also commercially available, may comprise one or more filters or other optical devices effective to filter or select radiation of particular wavelengths or to collect and collimate Raman scattered photons or radiation. These components are well-known and standard in the art of Raman spectroscopy.

The detector may be, but not limited to, a charge-coupled device, a photomultiplier tube, a photodiode or a photodiode array. The SERS system further may comprise the hardware and software necessary to analyze and display the spectral signature of the backscattered Raman light.

Thus, the present invention provides a method of fabricating the Dual-FON and Multi-FON substrates described herein. Generally, the method comprises depositing two or more of a continuous SERS-active metal layer over a support surface roughened by nanostructures coated thereon. Prior to deposition of a second, third, fourth, or fifth metal layer, the previously deposited metal layer is covered with a dielectric suitable for SERS substrates and SERs applications. The method is useful to fabricate substrates preferably having two to five metal layers, although more layers may be added.

It is contemplated that the Dual-FON and Multi-FON substrates provided herein are useful in a method of increasing, further enhancing or improving the signal intensity of a SERS signal emitted from any analyte. The analyte may be, but is not limited to, a compound, a composition or cell or other intracellular structure of interest suitable for analysis or identification by a SERS application. The analyte is disposed in contact with the outer layer of SERS-active metal comprising a Dual-FON or Multi-FON substrate. The presence of the two or more layers of a SERS active metal in combination with one or more optimal dielectric layers are effective to increase enhancement of a SERS Raman signal emitted by an analyte after illumination with a suitable wavelength of radiation over a SERS Raman signal emitted from the analyte in contact with an SFON substrate.

Embodiments of the present invention are better illustrated with reference to the Figures, however, such reference is not meant to limit the present invention in any fashion. The embodiments and variations described in detail herein are to be interpreted by the appended claims and equivalents thereof.

FIG. 1A is a not-to-scale depiction of the Dual-FON substrate. Dual-FON substrate 10 has a support structure 11, e.g., glass, quartz, metal foil, paper, a plastic surface, or wood upon which a layer of nanostructures 12 are uniformly coated. For example, the nanostructures may be alumina nanoparticles, silica spheres, titanium spheres, organic polymer spheres, or nanotubes having a uniform diameter of about 10 nm to about 10,000 nm. A SERS-active metal layer 13a of uniform thickness is deposited upon the nanostructures 12, as described in Examples 3 herein. Examples of a SERS-active metal may be, but not limited to, silver, gold, platinum, copper, ruthenium, rhodium, iron, or an alkali metal. The metal layer 13a may have a thickness of about 25 nm to about 1000 nm.

A dielectric 14 covers the SERS-active metal layer 13a. The dielectric may be formed, disposed or coated on the metal layer by any standard means known in the art determined by the type of dielectric used. Examples of a dielectric may be, but not limited to, an oxide of the SERS-active metal, silicon dioxide, titanium dioxide, or organic polymers. The dielectric may be formed via exposure of the SERS-active metal to air under ambient conditions, via vapor deposition or via chemical deposition. Exposure of the SERS-active metal to form the dielectric thereon is metal dependent such that exposure ranges from seconds to months. For example the metal layer 13a may be silver and the dielectric 14 is silver oxide formed by exposure of the silver to air at ambient conditions for about 50 hrs or less which forms an optimal silver oxide layer. A second SERS-active metal layer 13b is deposited uniformly, as was the first metal layer 13a, onto the dielectric 14. The second metal layer 13b also may have a thickness of about about 25 nm to about 1000 nm. It is contemplated that the total metal thickness, that is, the sum of both layer thicknesses, is about 50 nm to about 10,000 nm.

Figure 1B:
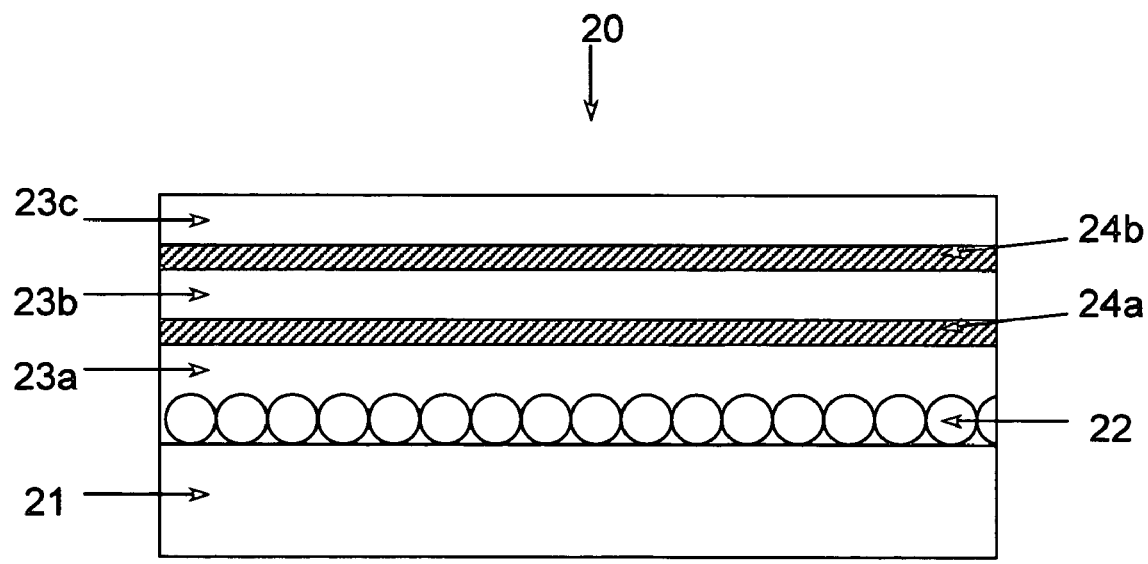

With continued reference to FIG. 1A, FIG. 1B is a not-to-scale depiction of a Multi-FON substrate. A Multi-FON substrate 20 is built on a Dual-FON structure 10. That is, Multi-FON substrate 20 structurally has at least a support structure 21, nanostructures 22, SERS-active metal layers 23a,b, and a dielectric 24a identical to the corresponding structural features of a Dual-FON substrate. A second dielectric 24b is formed or disposed or coated upon metal layer 23b as with dielectric 14. A third metal layer 23c is deposited upon dielectric 24b. As with a Dual-FON substrate each SERS-active metal layer may have a thickness of about about 25 nm to about 1000 nm. Furthermore, the present invention encompasses Multi-FON substrates with more than three metal layers, e.g., four or five layers, with a dielectric disposed between two adjacent metal layers. Multi-FON substrates may have a total metal thickness of about 50 nm to about 10,000 nm and with optimal dielectric layers are effective to enhance a SERS signal.

Figure 1C:
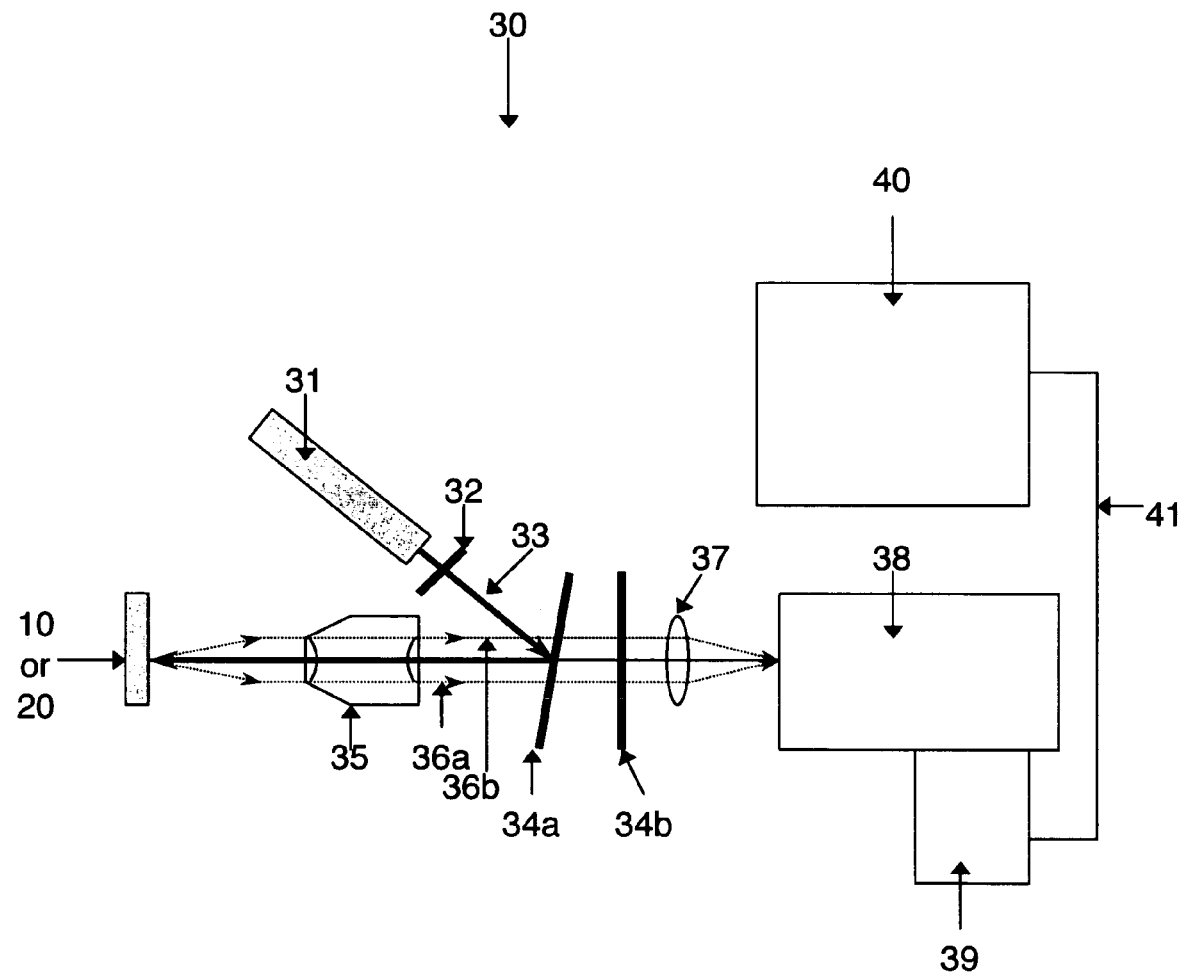

With continued reference to FIGS. 1A–1B, FIG. 1C is a schematic of one embodiment of a system for surface-enhanced Raman spectroscopy using the Dual-FON or Multi-FON SERS substrates. The system 30 uses an excitation source 31, such as a laser operating at 632.8 nm, with a band-pass filter 32 operably disposed to remove the plasma emission lines from the laser beam 33. After being filtered, the laser beam 33 is reflected off of a holographic notch filter 34a and focused onto the SERS substrate 10 or 20 using a 10× microscope objective 35. Microscope objective 35 also served to collect and collimate the backscattered SERS signals 36a, b, providing maximum excitation/collection efficiency. The collimated scattered light 36a, b, was then filtered by two holographic notch filters 34a, b to reject the Rayleigh scattered light, focused by a focusing lens 37, then dispersed by a spectrometer 38. This light was then detected using a detector 39, e.g., an intensified charge coupled device. An analyzed spectrum is displayed on a monitor 40, such as a computer monitor, operably connected via 41 to the detector 39.

The following examples are given for the purpose of illustrating various embodiments of the invention and are not meant to limit the present invention in any fashion.

EXAMPLE 1

Chemicals

Benzoic acid (Sigma), p-aminobenzoic acid (Sigma), terephthalic acid (Aldrich), brilliant cresyl blue (Sigma) and ethanol (Aldrich) were all used as received. Agglomerate-free alumina (Type CR15) was purchased from Baikowski International Corporation (Charlotte, N.C.). Silver particles were purchased from Kurt J. Lesker Company (Clairton, Pa.) with 99.99% purity.

EXAMPLE 2

Preparation of SERS Substrates

Glass microscope slides (VWR Scientific) used for SERS substrate supports were cut into rectangular strips (2.5 cm×1 cm) and cleaned with diluted nitric acid, distilled water and ethanol, as described previously (31) followed by air drying. Once the glass supports were cleaned, three drops of a 5% w/v suspension of 100 nm diameter alumina particles in distilled water were placed on the glass slide, covering the entire surface with alumina (32). The alumina-coated glass slide was then placed on a spin coater and spun for 5 seconds at 2500 rpm to uniformly spread the alumina particles over the slide surface. Following coating of the slide with alumina nanoparticles, a continuous layer of silver film was thermally evaporated on the slides to prepare traditional SFON substrates.

Dual-FON and Multi-FON substrates used in these studies were fabricated in a similar fashion to the SFON substrates. First, SFON substrates were created and exposed to ambient conditions for oxidation of silver surface before thermally coating additional continuous layer(s) of silver film on top of the oxidized SFON. For evaluation of all the substrates, 10 µL of a $2.0 \times 10^{-4}$ M solution of benzoic acid in ethanol was placed onto the substrates and SERS spectra were measured following evaporation of the ethanol.

EXAMPLE 3

Thermal Vacuum Evaporation System

Silver film deposition was performed using a vacuum evaporation system (Denton Vacuum; Model ExplorerTM-14). The alumina-coated glass slides were first placed in a homemade sample holder and mounted on a rotating disk 15 cm above the tungsten boat (R. D. Mathis company) containing 99.99% pure silver shot. During evaporation, the alumina coated substrates were rotated constantly to ensure an even coating of the silver film. A chamber pressure of approximately $3 \times 10^{-8}$ Torr was achieved prior to silver deposition and the deposition rate was controlled at approximately 1.8 nm/s. The thickness was monitored using an Inficon XTM/2 quartz crystal film thickness monitor mounted beside the sample holder.

EXAMPLE 4

SERS Measurement System and SEM/AFM Microscopy

The experimental measurement system used in this work is described supra and shown schematically in FIG. 1C. The components are a 10.0 mW CW HeNe laser (JDS Uniphase, Manteca, Calif.), operating at 632.8 nm, a band-pass filter, holographic notch filters (Kaiser Optical System), and a 10× microscope objective. The spectrometer is a 0.33 m spectrometer (Acton, model 300i) with a 600 grooves/mm grating and a 0.9 mm slit width, providing a spectral resolution of 13 $cm^{-1}$. This light was then detected using an intensified charge coupled device (ICCD, Roper Scientific, model PI-MAX). Control of the ICCD and spectral acquisition parameters were achieved using WinSpec 32 acquisition software and data was analyzed using Igor Pro 4.0 (WaveMetrics, Inc.).

Scanning electron microscopy (SEM) images were obtained with a JSM 5600 scanning electron microscope equipped with an energy dispersive x-ray (EDX-ray) mapping system (oxford ISIS) integrated with a Si(Li) light element analysis detector capable of performing analytical elemental analysis. Atomic force microscopy (AFM) images were acquired in both contact and non-contact modes using a Digital Instruments CP-II Scanning Probe Microscope.

EXAMPLE 5

Dual-FON SERS Substrate Enhancements

Comparison of the signal enhancement capabilities of these Dual-FON substrates to that of conventional SFON substrates was performed by spotting 10 µL of a $2.0 \times 10^{-4}$ M solution of benzoic acid in ethanol on several of each type of substrate and allowing it to spread over a 2.5 cm diameter circular area. By spotting this way a high degree of reproducibility in analyte delivery was achieved, comparable to other delivery methods, e.g., soaking the substrate in a dilute solution of the analyte, in terms of relative standard deviation from spot-to-spot, allowing for the direct comparison of signals obtained from substrate-to-substrate. After the ethanol was allowed to evaporate, SERS spectra were obtained using the measurement system described previously.

SFON substrates were prepared following a previously reported method (32) with a total silver layer thickness of 200 nm. These SFON substrates were then either analyzed immediately, or stored in vacuum until ready for analysis. The Dual-FON substrates used were fabricated by exposing SFON substrates to ambient conditions, i.e., room temperature air, humidity, etc., followed by the vapor deposition of a second layer of silver whose thickness was the same as the first layer. In the case of the Dual-FON substrates, each of the two layers applied was half the thickness of the silver applied to the SFON substrate, resulting in the same overall total silver thickness.

Figures 2A, 2B:
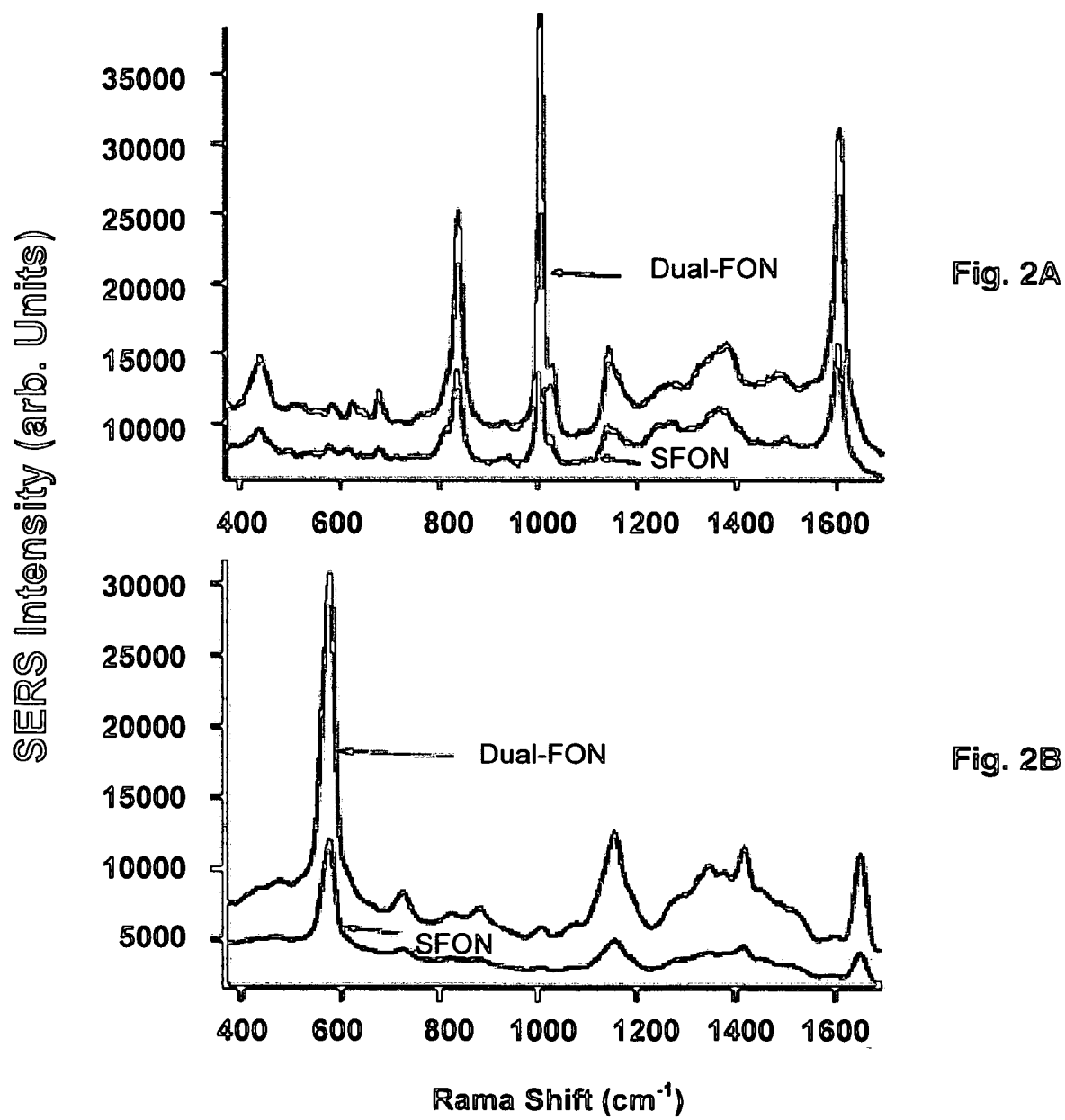
FIGS. 2A–2B show the SERS spectra of 54 ng benzoic acid (FIG. 2A) and 72 ng cresyl blue (FIG. 2B) on both SFON and Dual-FON substrates with total silver thickness of 200 nm.

A typical SERS spectrum of benzoic acid from each of the two types of substrates is shown in FIG. 2A for comparison. In each of these analyses, 500 ms exposure times were used with 100 accumulations being co-added in order to provide spectra with good signal-to-noise ratios. From these spectra, it can be seen that the SERS signals obtained on the Dual-FON substrates are approximately 250% greater than those obtained from SFON substrates while no apparent increase in the noise has occurred.

In order to ensure that this signal enhancement is not restricted to the functional groups and vibrational modes associated with benzoic acid, several other analytes also were evaluated with varying polarities and SERS active functional groups. FIG. 2B shows the SERS spectra of 10 µL of a $1 \times 10^{-4}$ M solution of brilliant cresyl blue spotted on both a SFON substrate (lower curve) and a Dual-FON substrate (upper curve). From these spectra, it can be seen that similar enhancement factors exist for this analyte as well. In fact, for all analytes investigated, Dual-FON substrates provided similar signal enhancements to that of the benzoic acid and cresyl blue. In addition to investigating different chemical species to ensure the general applicability of these substrates, excitation with 488 nm laser light from an argon ion laser was also investigated. In every case, similar results were obtained following 488 nm excitation as with 632 nm excitation demonstrating the wavelength independence of this Dual-FON enhancement.

EXAMPLE 6

Optimal Silver Thickness for Dual-FON Substrates

Following observation of the dual layer enhancement produced from Dual-FON substrates, determination of the optimal silver layer thickness for SERS enhancement was performed. In this study, SFON and Dual-FON substrates were prepared with various total silver thicknesses ranging from 25 nm to 600 nm, allowing investigation of both silver islands, as well as continuous silver films (thicknesses $\geq 100$ nm). In the case of the Dual-FON substrates, all substrates were prepared with two layers of equal thickness. For instance, for a total silver thickness of 200 nm, Dual-FON substrates were prepared by depositing two layers each 100 nm in thickness with a thin layer of silver oxide formed between them.

Figure 3:
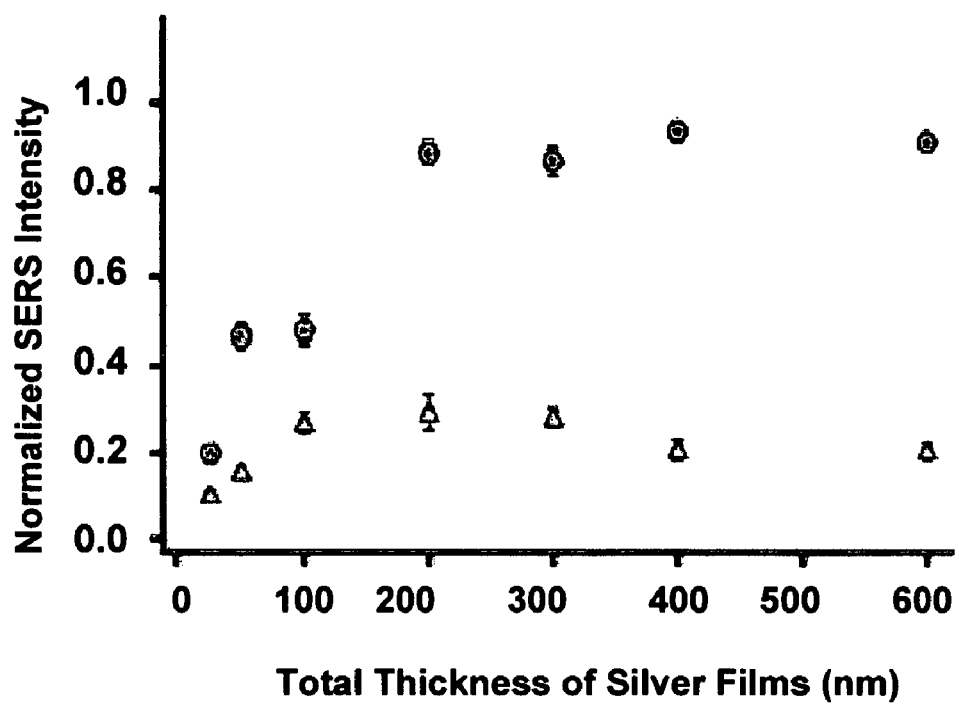
FIG. 3 shows the SERS intensity of 1002 $cm^{-1}$ peak of benzoic acid on SFON (triangles) and Dual-FON (circles) substrates with different total silver thicknesses. Each layer of the Dual-FON substrates is half of the total thickness displayed.

Once the substrates were fabricated, 10 µL of a $2.0 \times 10^{-4}$ M solution of benzoic acid was spotted onto each of the substrates, and the intensity of the 1002 $cm^{-1}$ ring breathing band was measured. FIG. 3 displays the results of this study, with each point representing the average of 8 measurements, after normalization to the maximum value measured for greatest signal measured. The error bars represent the noise of the measurement, as determined to be the standard deviation of the baseline. As can be seen from FIG. 3, the SERS signal intensities obtained on SFON substrates (triangles) increase with increasing thickness of silver films from 25 nm to 100 nm. In the region below 100 nm of silver thickness, the vapor deposited silver forms silver islands, which is obvious from SEM studies as well as the bluish color associated with the substrate upon looking at room lights through it. Beyond 100 nm thicknesses, the SERS intensities tend to level off and remain relatively constant, with a slight drop in signal intensity at 400 nm and greater. These results are consistent with previously reported results on SFON substrates.

For Dual-FON substrates (circles), significant increases in SERS signal intensities occurred for all of the substrates compared to their respective SFON substrates, even though the total thickness of silver films remained the same. In addition, it can also be seen from FIG. 3, that the Dual-FON substrates provide enhancements of 200–400%, relative to their corresponding SFON substrates, with the maximum enhancement occurring at total silver thicknesses of 200 nm or greater. This signal maximum at total silver thicknesses of 200 nm or greater suggests that the substrates with continuous films of silver provide more efficient signal enhancement than the substrates with discontinuous silver islands.

In addition to providing significant signal enhancements, these Dual-FON substrates also exhibit a high degree of reproducibility, both spot-to-spot and substrate-to-substrate. Evaluation of the spot-to-spot reproducibility was performed by measuring the signal intensity of the 1002 $cm^{-1}$ band of benzoic acid at five different locations over the spotted area of the substrate's surface and comparing the results. These analyses were performed on SFON and Dual-FON substrates having total silver thicknesses of 200 nm. For Dual-FON substrates, this 200 nm total thickness was obtained by applying two 100 nm thick layers to the alumina coated slides.

The spot-to-spot reproducibility, i.e., standard deviation of the 1002 $cm^{-1}$ signal intensity, of the SFON substrates was 9.3% and the spot-to-spot reproducibility of the Dual-FON substrates was 7.0%. Additionally, the substrate-to-substrate reproducibility, measured similarly over five different substrates, was found to be 9.4% and 8.8%, respectively, for the SFON and Dual-FON substrates. This demonstrates a slightly enhanced reproducibility of the Dual-FON substrates over the SFON substrates, as well as a significant improvement over the more typical reproducibility values of 15% or greater found in the literature for substrate-to-substrate variations. These values are consistent with those in the literature for their multilayered silver island substrates (37).

EXAMPLE 7

SERS Active Lifetime of Dual-FON Substrates

SERS active lifetimes also were characterized for Dual-FON substrates. It is well known that silver-based SERS substrates exhibit relatively short usable lifetimes. This short lifetime is especially a problem for silver island substrates, due to the rapid oxidation of the substrate's surface. Therefore, it is essential to verify the usable lifetime of silver-based substrates, in order to truly ensure that the substrate is viable for a variety of applications.

Figure 4:
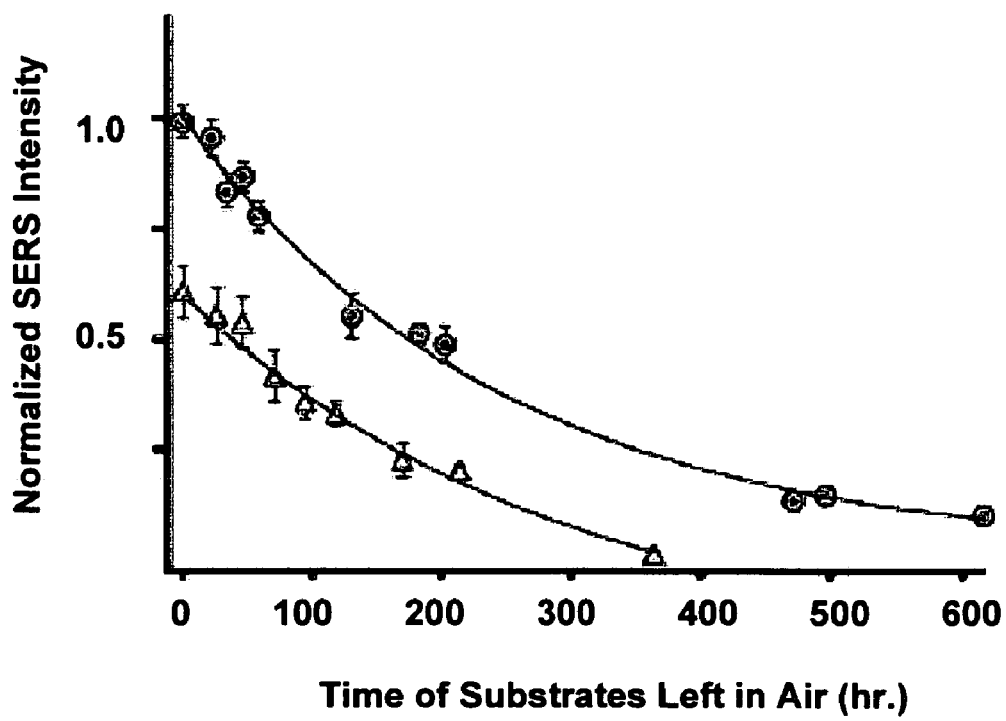
FIG. 4 shows the SERS active lifetime of SFON and Dual-FON substrates with total silver thicknesses of 200 nm. Signal intensities for both the Dual-FON (circles) and SFON (triangles) are measured from the 1002 $cm^{-1}$ band of benzoic acid after the substrate has been exposed to ambient conditions for different periods of time.

A batch of Dual-FON and SFON substrates having total silver thicknesses of 200 nm were prepared at the same time. The Dual-FON substrates were prepared by vapor depositing 100 nm of silver followed by a second layer of 100 nm after the first layer had been exposed to ambient conditions for only 5 minutes. Following fabrication, each of these substrates was then exposed to ambient conditions for a pre-determined period of time before being spotted with 10 μL of a $2.0 \times 10^{-4}$ M benzoic acid in ethanol solution, and then measured. Measurements were performed on each substrate immediately following evaporation of the ethanol solvent from the substrate's surface. Results from these measurements are shown in FIG. 4, in which each of the data points represents the average signal intensity of 15 measurements (3 substrates; 5 locations per substrate) of the 1002 $cm^{-1}$ band of benzoic acid. The error bars represent the standard deviation of those measurements.

From FIG. 4, it can be seen that as expected, the SERS signal intensity decreased with increased exposure time to air. In addition, it can also be seen that the decay rate of the signal intensity for the Dual-FON substrates (circles) is almost identical to that of the SFON substrates (triangles). In fact, these signals can be fitted within experimental error to exponential decay functions, shown as solid curves in FIG. 4, that provide statistically identical decay rates. However, due to the signal enhancement obtained from the Dual-FON substrates compared to SFON substrates, the SERS active lifetime of the substrates, defined as the time until the signal intensity of the measured sample reached a value of three times the intensity of the noise, is approximately twice that of the SFON substrates.

EXAMPLE 8

Substrate Morphology Studies

To better understand the reason for this two layer SERS enhancement, surface morphology studies were performed. It has long been known that SERS signal enhancements are sensitive to the size and shape of the roughened metal surface employed. In fact, changes in surface morphology have recently been suggested to be a primary reason for SERS signal enhancement in dual layer silver island film substrates in which depositing a second layer of silver islands provided surface structures of an optimal size (37). However, unlike this previous report, the Dual-FON substrates provided herein employ continuous layers of silver and rely on the underlying nanostructured surface to provide the roughness for the analysis. To ensure application of the additional layer of silver was not producing substrates with different surface roughnesses and geometries, scanning electron microscope (SEM) and atomic force microscope (AFM) images of the substrates were obtained for many substrates.

FIGS. 5A–5D show typical SEM and AFM images of two SERS substrates, each having a total silver film thickness of 200 nm. While the SEM images provide a visual picture of the overall surface structures, the AFM images provide topographical analyses, demonstrating the similarities of the two types of substrates. The SEM image in the upper left (FIG. 5A) is obtained from a 200 nm thick SFON substrat, and the SEM image in the upper right (FIG. 5B) is from a Dual-FON substrate prepared by depositing two 100 nm thick layers of silver. As can be seen from these images, the size and distribution of the particles that make up the roughened silver surface are visually similar for both the Dual-FON and SFON substrates.

Figure 5B:
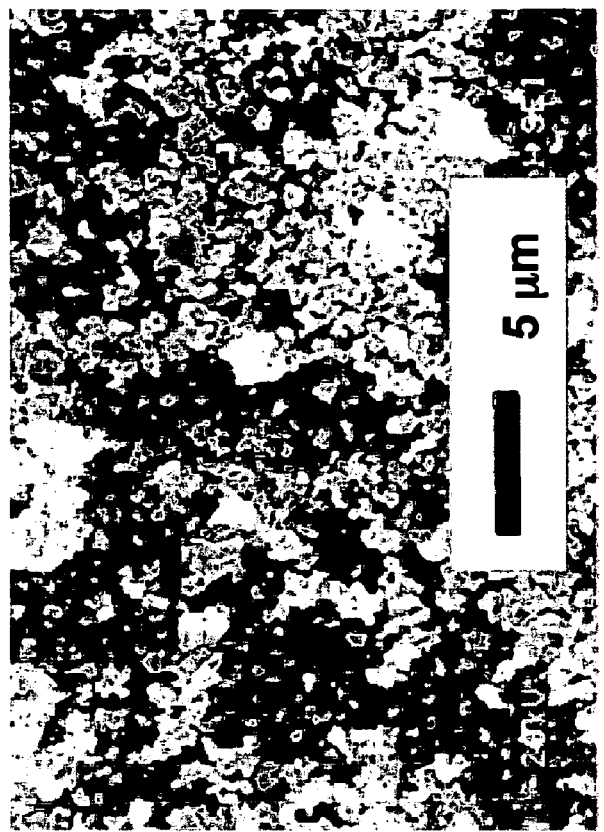
FIGS. 5A–5D show SEM images of SFON (FIG. 5A) and Dual-FON (FIG. 5B) substrates with total silver thicknesses of 200 nm and AFM images of the same SFON (FIG. 5C) and Dual-FON (FIG. 5D) substrates.
Figure 5A:
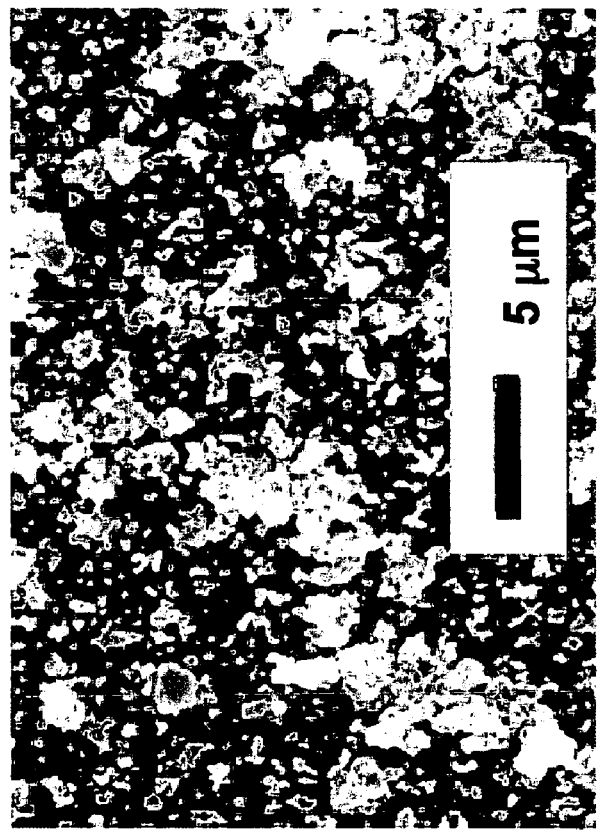
Figure 5D:
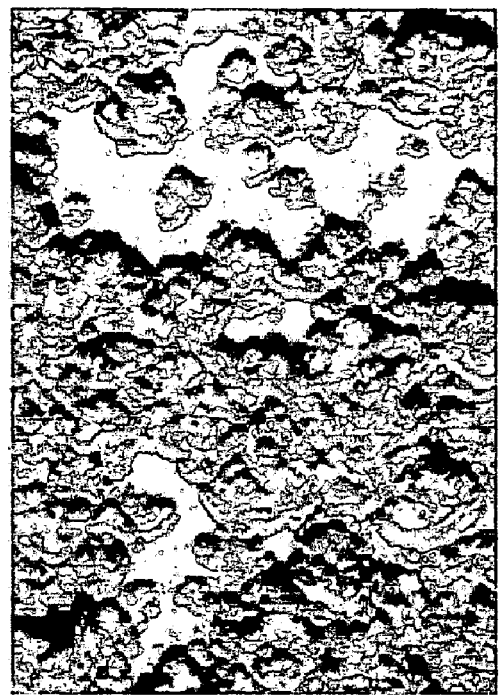
Figure 5C:
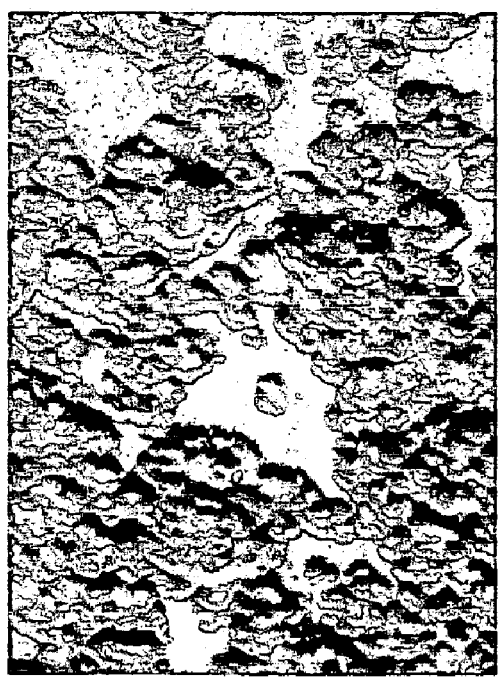

This conclusion is also confirmed by AFM images that were obtained from the same batch of SERS substrates as shown in FIGS. 5C–5D. From these AFM amplitude images, it can be seen that the surface particle size, roughness and distribution is similar for both the SFON (FIG. 5C) as well as Dual-FON (FIG. 5D) substrates. In addition, evaluation of the surface roughness and particle size and distribution were also performed using topographical surface analyses provided by the AFM measurements. Several parameters, which are characteristics of surface roughness, such as Ra (roughness average: the arithmetic average of the absolute values of the measured profile height deviations, $$Ra = \frac{1}{n}\sum_{i=1}^{n}|Z_i - \overline{Z}|,$$

Rpm and Rtm (mean values which are more representative of the entire profile, $$Rpm = \frac{1}{Y}\sum_{i=1}^{Y}<Z_{max} - \overline{Z}>_i,$$

$$Rtm = \frac{1}{Y}\sum_{i=1}^{Y}<Z_{max} - Z_{min}>_i\Bigg),$$

were evaluated.

The values of these parameters obtained from the SFON substrates measured were 66.4±23.2 nm, 124.9±65.8 nm, and 225.0±99.6 nm respectively, which are the same as those obtained from Dual-FON substrates, 56.5±16.1 nm, 123.8±37.8 nm, and 223.0±79.1 nm. While these values have a significant amount of variability associated with them, due to the alumina deposition process and alumina particle size distribution, they confirm that the surface roughness of the substrates is not varied by depositing a second continuous layer of silver. Therefore, this SERS enhancement arises from another mechanism.

EXAMPLE 9

Optimization of Silver Oxide Layer

Due to the rapid oxidation of silver under ambient conditions and the lack of surface roughness differences between the SFON and Dual-FON substrates, it is apparent that the formation of silver oxide between the two layers must play a critical role in the signal enhancement mechanism. Therefore, a systematic study of the effect of oxidation on the under-layer of the Dual-FON substrate was performed to optimize the signal enhancement abilities of the substrates. A series of 100 nm thick SFON substrates were prepared. Following deposition of silver on the alumina coated substrates they were exposed to atmospheric conditions for various amounts of time, ranging from 0–480 hours prior to coating the second layer of silver on the substrates. Immediately following deposition of the second silver layer, 10 μL of a 2.0×10$^{-4}$ M solution of benzoic acid was placed on the substrates, and SERS measurements were obtained following evaporation of the ethanol.

Figure 6:
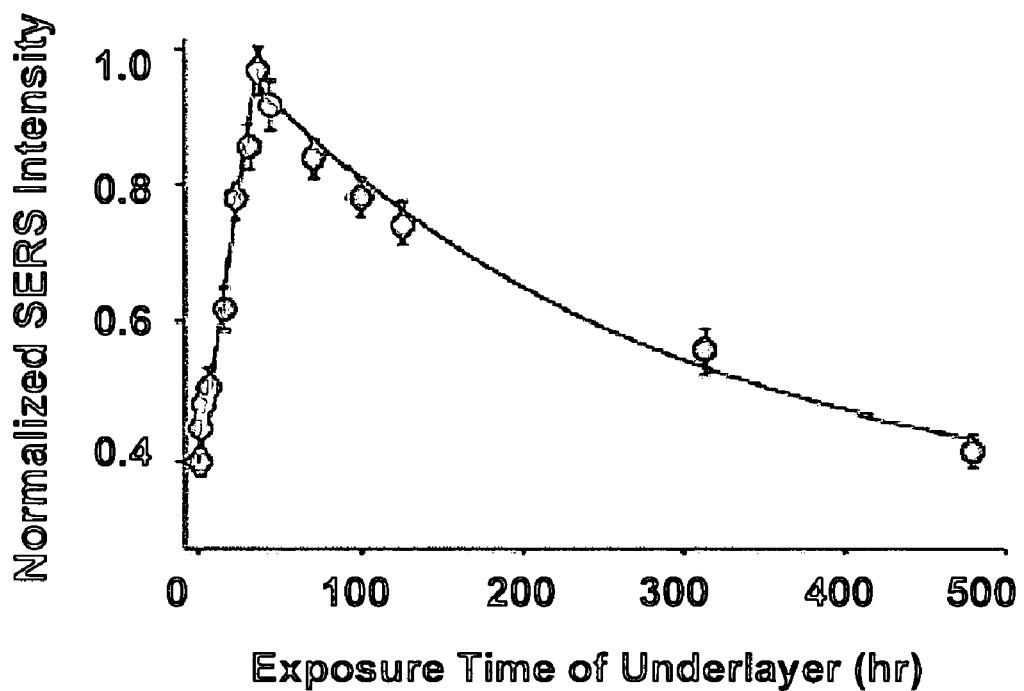
FIG. 6 shows the SERS intensity of 1002 $cm^{-1}$ peak of benzoic acid on Dual-FON substrates following different exposure times of the silver under-layer to air. Total silver film thickness is 200 nm.

The results of these measurements are shown in FIG. 6, where each data point represents the average signal intensity of the 1002 cm$^{-1}$ band of benzoic acid from five different locations on the three substrates measured for each time point. Two distinct regions are apparent. Between 0–48 hours of exposure of the under-layer of silver to ambient conditions, the SERS signal intensity dramatically increases, resulting in a five fold enhancement in signal relative to 0 hours exposure. At 0 hours of exposure of the silver under-layer to air, the substrate corresponds to an SFON substrate, as the vacuum on the chamber was never broken before depositing the second 100 nm of silver. In addition, the maximum signal, which occurs at 48 hours of exposure of the under-layer to air provides a signal enhancement of approximately 2.5 fold when compared to the substrates exposed to air for only 3 minutes. This difference in silver oxidation can also be seen when comparing FIGS. 3 and 4, in which substrates prepared in these studies were prepared with underlayer exposure times of approximately 48 hours and 5 minutes respectively. After exposure of the under-layer of silver to air for longer than 48 hours, the signal intensity decreases significantly, until reaching a point similar to that of a 3 minute exposure beyond 500 hours of exposure of the under-layer.

Thus, the role of the silver oxide layer is important in determining the enhancement of the dual layer substrates. It is contemplated that the silver oxide layer that forms between the two silver layers acts as an insulator, allowing two individual electromagnetic (EM) fields to be produced, one in each layer, following excitation. These two EM fields can then interact to reinforce each other, providing a long range EM enhancement to any sample placed on the upper layer. Due to the relatively thick layers of silver, i.e., 100 nm, that were deposited during the fabrication of these substrates, direct interaction of the silver under-layer with the analyte molecules through a chemical enhancement mechanism is precluded, as the SERS signal would decrease by half for every 7 Å between the surface and analyte (40).

This long range EM enhancement mechanism is consistent with the results obtained from these silver oxide studies. For initial exposure times of the under-layer to air, between 0–48 hours, the oxidation of the silver under-layer surface is taking place. Initially, at times between 0–48 hours, the two layers of silver still are capable of direct silver-silver contact between them, reducing the ability to form two separate electromagnetic fields associated with each layer. As the under-layer exposure time increases, the separation of the two silver layers is increased, increasing the strength of the two separate EM fields. At 48 hours of exposure, the surface of the under-layer is sufficiently oxidized to reduce direct silver-silver contact between the two layers, thereby allowing the two completely separate electromagnetic fields to be produced that are close enough to reinforce one another.

At under-layer exposure times greater than 48 hours, the silver oxide layer becomes sufficiently thick enough to reduce the electromagnetic interaction of the two fields, thus decreasing the overall strength of the SERS signal. Further evidence suggesting this increased separation distance as the reason for SERS signal reduction is provided by the decay rate of the SERS signal with under-layer exposure time after the optimal 48 hours of exposure. This decay rate is the same as that measured in the SERS active lifetime studies (FIG. 4), in which the reduction in signal is due to increased separation distance of the analyte from the SERS metal surface, due to silver oxide formation.

EXAMPLE 10

Multilayer Enhancement

Due to the significant signal-to-noise enhancements achieved with Dual-FON substrates, Multi-FON substrates were fabricated and investigated to determine whether or not further enhancement could be achieved by depositing additional layers of silver. Multi-FON substrates were prepared similarly to the Dual-FON substrates, with 100 nm thick layers of silver being deposited after exposing the previously deposited layer to air for 3 minutes. After coating of the final layer, samples were deposited on the substrate, and measurements were performed immediately following evaporation of the solvent.

Figure 7:
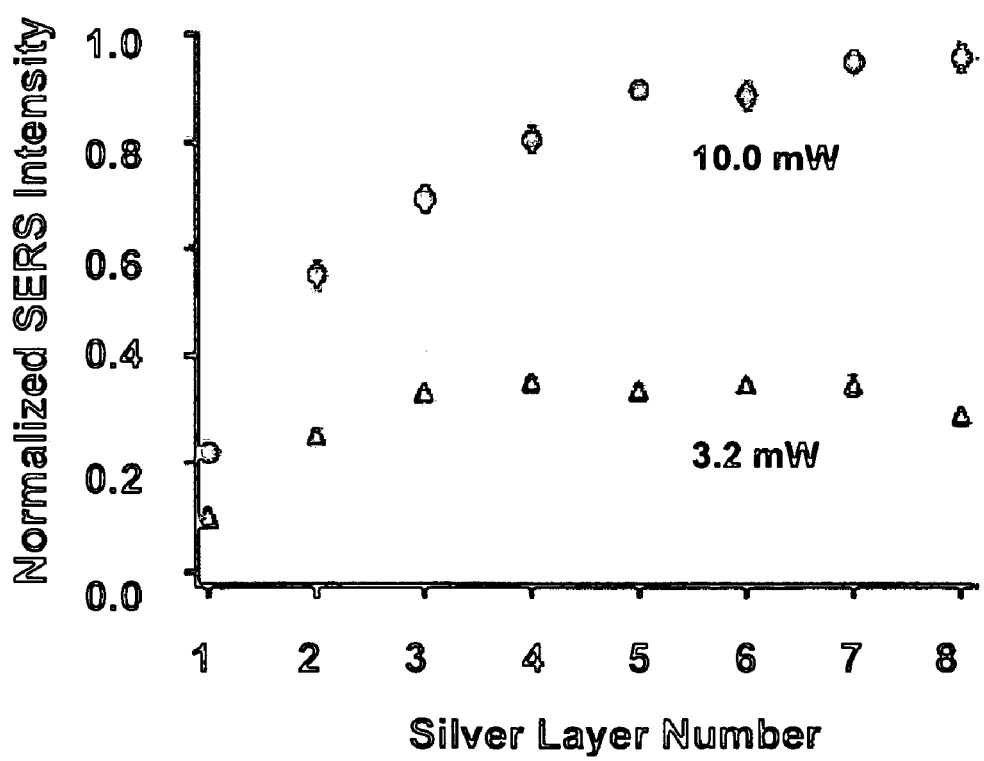
FIG. 7 shows the SERS intensity of 1002 $cm^{-1}$ peak of benzoic acid on multi-layered substrates, with each silver layer having a thickness of 100 nm, following 10.0 mW (circle) and 3.2 mW excitation (triangle).

FIG. 7 shows the effect of multiple layers of silver on the SERS signal intensity of the 1002 cm$^{-1}$ band of benzoic acid for two different excitation laser powers, 10 mW (circles) and 3.2 mW (triangles). For these analyses, 10 μl of a 2.0×10$^{-4}$ M solution of benzoic acid was spotted on the substrate and allowed to spread out in a circular area with a diameter of 2.5 cm. 3.2 mW excitation was obtained by placing a neutral density filter in the beam path of the laser, thereby ensuring that any differences between the two sets of analyses were due solely to laser power and not alignment, beam profile or any other characteristics that might arise from the use of a different laser source. The signal intensities plotted on the y-axis represent the average intensity obtained from 15 measurements, i.e., 5 different locations on 3 different substrates. The error bars represent the standard deviation of these averages. The results of these measurements have been normalized to provide a rapid means of comparing the relative signal strength of the different substrates.

From this figure, it can be clearly seen that as the number of silver layers increases the signal intensity increases as well, for both excitation powers. For the 3.2 mW measurements, the SERS signal intensity increases with each additional layer applied until leveling off after 3 layers of silver. When going from a single layer SFON substrate to a two layer Dual-FON substrate a signal enhancement of approximately 210% is achieved which is consistent with previous results obtained during Dual-FON studies. Upon applying a third layer of silver, the SERS signal intensity increases again, providing a total enhancement of 383%. However, application of additional layers of silver has no further effect on the SERS enhancement. One potential explanation for the leveling off of this enhancement, is that the excitation power used, i.e., 3.2 mW, cannot penetrate deep enough into the substrate to effectively interact with silver layers deeper than the third layer.

A second series of measurements were performed in which the samples were excited with 10 mW from the same HeNe laser. The results of these measurements are also shown in FIG. 7 (circles). From these measurements, it can be clearly seen that a maximum multi-layer enhancement of approximately 500% can be achieved following excitation with 10 mW of laser power. In addition, this data shows that SERS signal enhancements continue to occur until five layers of silver are applied to the substrate. Beyond this point the signal levels off, as it did at three layers following excitation with 3.2 mW. These results are consistent with the theory that increased laser power allows for excitation of additional under-layers of silver, thereby increasing the SERS signal through the multiple reinforcement of the electromagnetic field of the outermost layer of silver. By combining the optimal layer geometry, i.e., 5 layers using 10 mW of laser power, with the optimal silver oxide separation layer between each silver layer, enhancements of 1000% can be achieved.

EXAMPLE 11

Silica Sphere Based Multi-Layer Enhancements

To ensure that this multi-layer enhancement could be used for improving various SFON substrates, different size silica spheres were used for providing the roughness instead of alumina particles. Silver layer thicknesses of 100 nm were applied to the silica sphere based substrates, as with alumina based substrates. Dual-FON substrates were made by exposing the SFON substrates to ambient atmosphere for approximately 48 hours followed by the vapor deposition of another silver film layer whose thickness was same as the first layer. SERS signals of 10 μl of 10$^{-4}$ M benzoic acid were then evaluated on these substrates, which were fabricated over different sizes of silica spheres with diameters ranging from 100 nm to 4500 nm.

Figure 8:
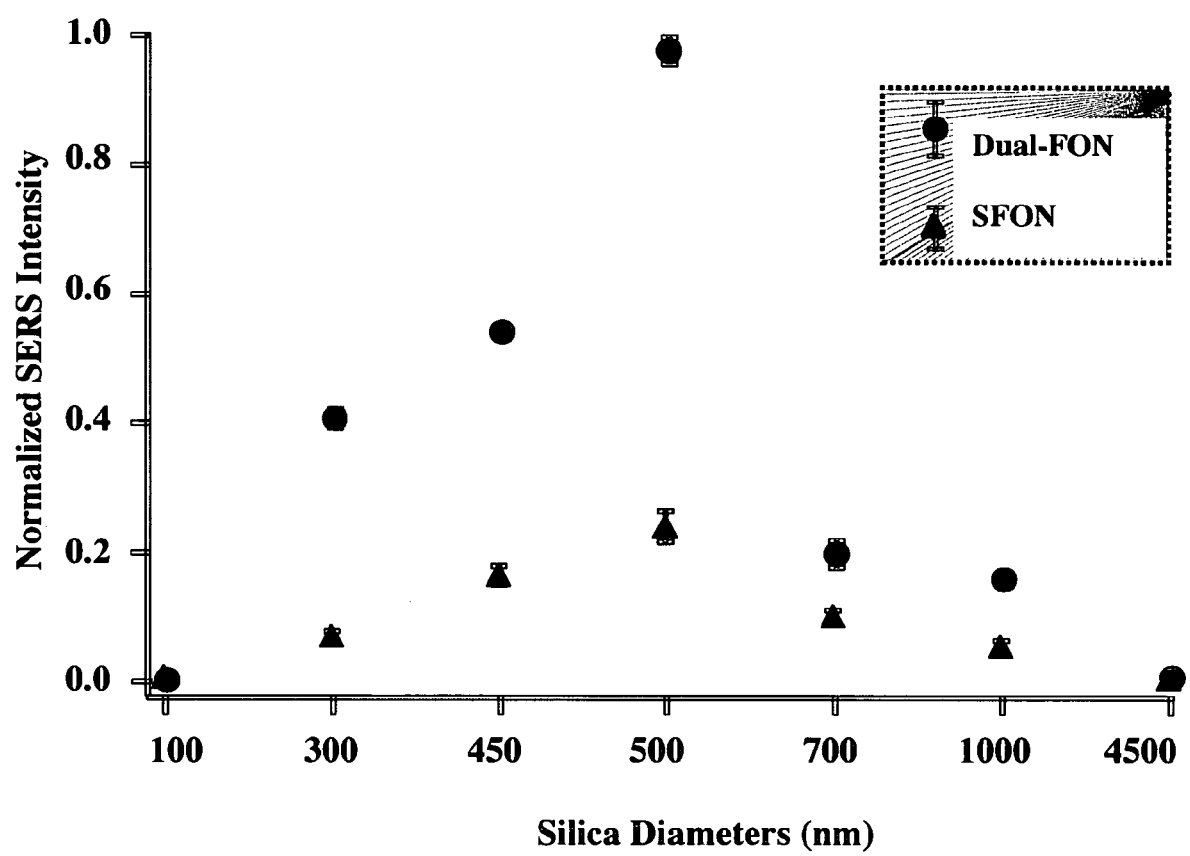
FIG. 8 demonstrates normalized SERS enhancements on Dual-FON and SFON substrates with same total silver thickness of 200 nm and different diameters of silica spheres.

FIG. 8 shows a comparison of the SERS intensities obtained on SFON and Dual-FON substrates with the same silver total thickness of 200 nm. From this plot, it is evident that Dual-FON substrates almost always produce more enhancement than SFON substrates, except for the two extreme sphere sizes, 100 nm and 4500 nm. For these two sizes, SERS signals could barely be detected for either architecture. For substrates fabricated on silica spheres with diameters ranging between 300–500 nm, Dual-FON substrates produced approximately 500%–600% times enhancements over the SFON substrates. For substrates fabricated on silica spheres with diameters larger than 500 nm, enhancements obtained from Dual-FON substrates were still higher than those for the SFON substrates, only approximately 200% times. Based on all of the dual-layer silver film substrates prepared, using 500 nm diameter silica sphere substrates produced the best SERS enhancements, with absolute enhancement factors of 1.9×10$^6$. By applying multiple silver layers, even greater enhancements up to an order of magnitude could be observed, compared to optimized SFON substrates (data not shown).

THE FOLLOWING REFERENCES ARE CITED HEREIN

1. Fleischmann, et al. Chem. Phys. Lett. 26, 163, (1974).
2. Chourpa, et al. FEBS Lett 397, 6, (1996).
3. Shafer-Peltier, et al. J. Am. Chem. Soc. 125, 588, (2003).
4. Vo-Dinh, et al. J. Raman Spectrosc. 33, 511, (2002).
5. Bao, et al. J. Raman Spectrosc. 32, 227, (2001).
6. Ozeki, et al. J. Sol. Chem. 10 861, (2000).
7. Brolo, et al. J. Phys. Chem. B 106, 5982, (2002).
8. M. J. Weaver, J. Raman Spectrosc. 33, 309, (2002).
9. Litorja, et al. J. Phys. Chem. B 105, 6907, (2001).
10. Taranenko, et al. J. Raman Spectros. 27, 379 (1996).
11. Premasiri, et al. J. Raman Spectros. 32, 919, (2001).
12. S. Nie and S. R. Emory, Science 275, 1102 (1997).
13. Kneipp, et al. Phys. Rev. Lett. 78, 1667 (1997).
14. Deckert, et al. Analytical Chemistry 70, 2646, (1998).
15. W. E. Doering and S. Nie, J. Phys. Chem. B 106, 311, (2002).
16. J. Gersten and A. Nitzan, J. Chem. Phys. 73, 3023, (1980).
17. M. Kerker, Acc. Chem. Res. 17, 271 (1984).
18. A. Otto, "Surface-Enhanced Raman Scattering: 'Classical' and 'Chemical' Origins," *Light Scattering in Solids IV: Electronic Scattering, Spin Effects, SERS, and Morphic Effects*, M. Cardona and G. Guntherodt. Eds., (Springer-Verlag Berlin Heidelberg, New York, 2984), Vol. 54, P. 289.

19. Wang, et al. J. Raman Spectros. 33, 125, (2002).
20. M. Muniz-Miranda, J. Raman Spectrosc. 31, 637, (2000).
21. N. Leopold and B. Lendl, J. Phys. Chem. B 107, 5723, (2003).
22. Lyon, etal. Anal. Chem. 70, 5177, (1998).
23. Zhen, et al. J. Phys. Chem. B. 106, 1019, (2002).
24. Hoogvliet, et al. Anal. Chem. 72, 2013, (2000).
25. A. Michota and J. Bukowska, J. Raman Spectros. 34, 21, (2003).
26. G. Xue and J. Dong, Anal. Chem. 63, 2393, (1991).
27. Boo, et al. Chem. Phys. Lett. 120, 301 (1985).
28. F. Ni and T. M. Cotton, Anal. Chem. 58, 3159, (1986).
29. Kwon, et al. J. Phys. Chem. B 103, 9610, (1999).
30. Chen, et al. Phys. Rev. B 51, 4507, (1995).
31. Bello, et al. Anal. Chem. 61, 1779 (1989).
32. Bello, et al. Appl. Spectrosc. 43, 1325, (1989).
33. A. M. Alak and T. Vo-Dinh, Anal. Chem. 61, 656, (1989).
34. H. Li and B. M. Cullum, SPIE Proc. 5261, 142, (2003).
35. Kneipp, et al. Phys. Rev. E 57, R6281, (1998).
36. Duyne, etal. J. Chem. Phys. 99, 2101, (1993).
37. Leverettee, et al. J. Phys. Chem. B 106, 8747 (2002).
38. Mulvaney, et al. J. of Raman Spectrosc. 34, 163, (2003).
39. Dick, et al. J. Phys. Chem. B 106, 853, (2002).
40. Ye, et al. J. Phys. Chem. B 101, 8221, (1997).

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A substrate for surface enhanced Raman spectroscopy (SERS), comprising:
   a support material having a flat surface coated with a plurality of nano-structures;
   two or more layers of a SERS-active metal deposited thereon; and
   one or more layers of a dielectric on one or more layers of said SERS-active metal.

2. The SERS substrate of claim 1, wherein said support material is glass, quartz, metal foil, paper, a plastic surface, or wood.

3. The SERS substrate of claim 1, wherein said nano-structures are alumina nanoparticles, silica spheres, titanium spheres, organic polymer spheres, or nanotubes.

4. The SERS substrate of claim 1, wherein said nano-structures have a diameter of about 10 nm to about 10,000 nm.

5. The SERS substrate of claim 1, wherein said SERS-active metal is silver, gold, platinum, copper, ruthenium, rhodium, iron, or alkali metal.

6. The SERS substrate of claim 1, wherein said dielectric is an oxide of the SERS-active metal, silicon dioxide, titanium dioxide, or organic polymers.

7. The SERS substrate of claim 1, wherein said dielectric is formed via exposure of the SERS-active metal to air under ambient conditions, via vapor deposition or via chemical deposition.

8. The SERS substrate of claim 7, wherein exposure of the SERS-active metal to form the dielectric thereon is metal dependent such that exposure ranges from seconds to months.

9. The SERS substrate of claim 1, wherein said two or more SERS-active metal layers each have a thickness of about 25 nm to about 1000 nm.

10. The SERS substrate of claim 1, wherein a total thickness of said two or more SERS-active metal layers is about 50 nm to about 10,000 nm.

11. The SERS substrate of claim 1, said substrate comprising two to five SERS-active metal layers and one to four dielectric layers.

12. A system for surface enhanced Raman spectroscopy (SERS), comprising:
    the SERS substrate of claim 1;
    a radiation source having optical power effective to penetrate the SERS-active metal layers of said SERS substrate;
    a spectrometer effective for collecting and dispersing collimated back scattered Raman radiation;
    a detector for detecting said dispersed radiation;
    a first set of optics for directing incident radiation from said radiation source to one or more SERS-active metal surfaces comprising the substrate; and
    a second set of optics for collimating and directing back scattered Raman radiation emitted from the substrate to the spectrometer.

13. The SERS system of claim 12, further comprising:
    means for analyzing and displaying said detected Raman radiation as a Raman spectral image.

14. The SERS system of claim 12, wherein said radiation source is a laser producing more than 1 µW of power to about 5 W of power.

15. The SERS system of claim 12, wherein said detector is an intensified charge coupled device, a photomultiplier tube, a photodiode or a photodiode array.

16. The SERS system of claim 12, wherein said first set of optics and said second set of optics comprise means to collimate radiation and one or more filters or lenses operably disposed between the radiation source, the SERS substrate and the spectrometer.

17. A method for increasing a Raman signal intensity during surface-enhanced Raman spectroscopy, comprising:
    providing the SERS substrate of claim 1;
    bringing an analyte into effective contact with the SERS substrate; and
    illuminating said analyte with radiation from a source of sufficient power to optically penetrate the SERS-active metal layers comprising the SERS substrate to increase a SERS signal intensity emitted therefrom; wherein said increase in signal intensity is a result of the total increase in electromagnetic field within said SERS-active metal layers.

18. The method of claim 17, further comprising:
    collecting and detecting said increased SERS signal for spectral analysis thereof; and
    generating a signature spectrum for the analyte based on the spectral analysis.

19. The method of claim 17, wherein said radiation source is a laser producing more than 1 µW of power to about 5 W of power.

20. A method of fabricating a substrate for surface-enhanced Raman spectroscopy (SERS), comprising:
 coating a support surface with a plurality of nano-structures suitable for a SERS application;
 depositing a continuous layer of a SERS-active metal over said nano-structures;
 covering said deposited continuous layer with a dielectric; and
 depositing a continuous layer of the SERS-active metal over said dielectric.

21. The method of claim 20, further comprising repeating the steps of covering the deposited continuous layer with a dielectric and depositing a continuous SERS-active metal layer thereon.

22. The method of claim 21, wherein said steps are repeated one to three times.

23. The method of claim 20, wherein covering the SERS-active metal layer with a dielectric comprises exposing said SERS-active metal layer to air at ambient conditions to form a dielectric thereon or depositing said dielectric via vapor deposition or chemical deposition.

24. The method of claim 23, wherein exposure of the SERS-active metal to form the dielectric thereon is metal dependent such that exposure ranges from seconds to months.

25. The method of claim 20, wherein said support surface is glass, quartz, metal foil, paper, a plastic surface, or wood.

26. The method of claim 20, wherein said nanostructures are alumina nanoparticles, silica spheres, titanium spheres, organic polymer spheres, or nanotubes.

27. The method of claim 20, wherein said nanostructures have a diameter of about 10 nm to about 10,000 nm.

28. The method of claim 20, wherein said SERS-active metal is silver, gold, platinum, copper, ruthenium, rhodium, iron, or alkali metal.

29. The method of claim 20, wherein each layer of SERS-active metal has a diameter of about 25 nm to about 1000 nm.

30. The SERS substrate of claim 20, wherein said dielectric is an oxide of a SERS-active metal, silicon dioxide, titanium dioxide, or organic polymers.

* * * * *